(12) United States Patent
Meiere

(10) Patent No.: US 7,244,858 B2
(45) Date of Patent: Jul. 17, 2007

(54) ORGANOMETALLIC PRECURSOR COMPOUNDS

(75) Inventor: Scott Houston Meiere, Williamsville, NY (US)

(73) Assignee: Praxair Technology, Inc., Danbury, CT (US)

( * ) Notice: Subject to any disclaimer, the term of this patent is extended or adjusted under 35 U.S.C. 154(b) by 118 days.

(21) Appl. No.: 11/037,085

(22) Filed: Jan. 19, 2005

(65) Prior Publication Data

US 2005/0215805 A1 Sep. 29, 2005

(51) Int. Cl.
*C07F 11/00* (2006.01)

(52) U.S. Cl. .......................... 556/58; 556/40; 556/41; 556/59

(58) Field of Classification Search ................ 556/58, 556/40, 41, 59, 60
See application file for complete search history.

(56) References Cited

U.S. PATENT DOCUMENTS

| | | | |
|---|---|---|---|
| 6,420,583 B1 | 7/2002 | Lienhard et al. | 556/136 |
| 6,521,772 B1 | 2/2003 | Lienhard et al. | 556/136 |
| 2004/0010158 A1 | 1/2004 | Meire et al. | 556/136 |

OTHER PUBLICATIONS

Huicai Zhong et al., "Properties of Ru—Ta Alloys as Gate Electrodes For NMOS and PMOS Silicon Devices" *IEDM 2001*20.5.1.
L.R.C. Fonseca et al., "First-Principles Calculation of the Work Function of Metals on High-K Metal Oxides" *Fall MRS 2003*E4.3.
Matous Mrovec et al., Schottky Barriers at Transition-metal/Strontium—titanate Contacts, *Fall MRS 2003 E4.2.*
Gordon et al., "Low-temperature atmospheric-pressure metal-organic chemical vapor deposition of molybdenum nitride thin films", *Thin Solid Films* 1996 288 116.
Van den hove et al, "Lithography for sub-90nm applications", *IEEE* 2002.
Rausch et al., Functionally Substituted Derivatives of ($n^5$ -$C_5H_5$)M(CO)$_2$NO (M =Cr, Mo, W) *Organometallics*1983, 2, 1523.
Legzdins et al., Dicarbonyl ($\eta^5$-Cyclopentadienyl)Nitrosyl Complexes of Chromium, Molybdenum, and Tungsten, *Inorg. Synth*, 1990, 28, 196.

*Primary Examiner*—Thurman K. Page
*Assistant Examiner*—MLouisa Lao
(74) *Attorney, Agent, or Firm*—Gerald L. Coon

(57) ABSTRACT

This invention relates to organometallic precursor compounds represented by the formula (L)M(L')$_2$(NO) wherein M is a Group 6 metal, L is a substituted or unsubstituted anionic ligand and L' is the same or different and is a π acceptor ligand, a process for producing the organometallic precursor compounds, and a method for producing a film, coating or powder from the organometallic precursor compounds.

40 Claims, No Drawings

US 7,244,858 B2

ORGANOMETALLIC PRECURSOR COMPOUNDS

FIELD OF THE INVENTION

This invention relates to organometallic precursor compounds represented by the formula (L)M(L')$_2$(NO) wherein M is a Group 6 metal, L is a substituted or unsubstituted anionic ligand and L' is the same or different and is a π acceptor ligand, a process for producing the organometallic precursor compounds, and a method for producing a film or coating from the organometallic precursor compounds.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition chemical compound, is decomposed thermally, chemically, photochemically or by plasma activation, to form a thin film having a desired composition. For instance, a vapor phase chemical vapor deposition precursor can be contacted with a substrate that is heated to a temperature higher than the decomposition temperature of the precursor, to form a metal or metal oxide film on the substrate. Preferably, chemical vapor deposition precursors are volatile, heat decomposable and capable of producing uniform films under chemical vapor deposition conditions.

The semiconductor industry is currently considering the use of thin films of various metals for a variety of applications. Many organometallic complexes have been evaluated as potential precursors for the formation of these thin films. A need exists in the industry for developing new compounds and for exploring their potential as chemical vapor deposition precursors for film depositions.

Molybdenum materials are being considered for a number of applications in the electronics industry for next generation devices, including electrode, barrier, and lithography. Similar to the interest in tuning a material by creating an alloy of a n-type and p-type metal in different ratios (as exemplified by the work by Misra V. et al. at North Carolina State (IEDM 2001 20.5.1)), molybdenum can be tuned with nitrogen incorporation and/or deposition orientation to generate a similar effect (with the advantage of a single, less expensive source). The work function of molybdenum can thus be adjusted significantly (Fonseca, L. R. C., Fall MRS E4.3, 2003 and Mrovek, M., Fall MRS E4.2, 2003).

Another interest in molybdenum materials is for barrier applications (e.g., Cu). Molybdenum nitrides are candidates for this application (Gordon R. et al., *Thin Solid Films* 1996 288 116). Molybdenum films also have applications in the area of lithography, with potential utility for the engineering of projection lens systems for photolytical patterning of substrates for extreme ultra-violet lithography (EUVL) at the 45 nm technology node (Van den hove, L. IEEE 2002).

The industry movement from physical vapor deposition to chemical vapor deposition and atomic layer deposition processes due to the increased demand for higher uniformity and conformality in thin films has lead to a demand for suitable precursors for future semiconductor materials. For molybdenum, the traditional chemical vapor deposition precursors have been Mo(CO)$_6$ and (Et$_x$C$_6$H$_{6-x}$)$_2$Mo (a mixture of bis(ethylbenzene)molybdenum species). The former suffers from being a solid up to its decomposition point of 150° C., and the latter, although a liquid, does not have a high vapor pressure (~0.1 torr at 160° C.) and may deliver inconsistently due to the various species present.

(C$^7$H$_8$)Mo(CO)$_3$ is also available, but is a solid (mp=100° C.), and lacks sufficient thermal stability to be a highly desirable candidate.

Building from Mo(CO)$_6$, replacing three CO's with a cyclopentadienyl (Cp) group seems logical since many Cp systems are known chemical vapor deposition precursors and Cp allows excellent tunability for achieving liquid systems. However, [CpMo(CO)$_3$]$^-$ exists as an anion, and therefore is not sufficiently volatile (note, the dimer of this system is neutral, but has little volatility due to the increased molecular weight). Changing Cp to a similar neutral six electron donor would seem a logical progression, thus yielding the aforementioned (C$_7$H$_8$)Mo(CO)$_3$. Although this compound is neutral with perhaps adequate volatility, the other issue with these tricarbonyl systems is their instability. The lack of enough strong π-acids, like CO, render the material very electron rich, and make the complex susceptible to premature decomposition. Two potential pathways are a 'ring-slip' for the cycloheptatriene ligand from an η$^6$ six electron donor to an η$^4$ four electron donor (alleviating the electron density on molybdenum) or loss of a hydride from the cycloheptatriene ligand creating an aromatic system and creating a less donating environment and a molybdenum cation. Another known molecule, (C$_6$H$_6$)Mo(CO)$_3$, suffers from similar instability issues.

While the unsubstituted cyclopentadienyl compound, i.e., CpMo(CO)$_2$(NO), and the methyl substituted cyclopentadienyl compound, i.e., (MeCp)Mo(CO)$_2$(NO), are known materials (Legzdins, P. et al. Inorg. Synth. 1990, 28, 196 and references therein and Rausch, M. D. et al. Organometallics 1983, 2, 1523 and references therein), there appear to be no prior teachings or work relating to the use of these compounds as precursors for chemical vapor deposition or atomic layer deposition.

In developing methods for forming thin films by chemical vapor deposition methods, a need continues to exist for chemical vapor deposition precursors that preferably exhibit dual metal gate applications, are liquid at room temperature, have relatively high vapor pressure and can form uniform films. Therefore, a need continues to exist for developing new compounds and for exploring their potential as chemical vapor deposition precursors for film depositions. It would therefore be desirable in the art to provide a chemical vapor deposition precursor having dual metal gate applications, a high vapor pressure and that can form uniform films.

SUMMARY OF THE INVENTION

This invention pertains to chemical vapor deposition and atomic layer deposition precursors for next generation devices, specifically molybdenum-containing precursors that exhibit dual metal gate applications. Molybdenum (Mo) is a 'mid-gap' material (i.e., it possesses an intermediate work function between n-type (~4.0 eV) and p-type (~5.0 eV) species), and depending on how it is deposited can serve as both an n- and p-type electrode, as well as for barrier and lithography applications. The physical location of molybdenum on the periodic table between n-type materials on the left (e.g., Ti, Zr, Hf, Ta) and p-type on the right (e.g, Ni, Pd, Pt, Ir) helps to demonstrate its flexibility.

As an advantage over the n-type species, molybdenum metal is typically easier to deposit than the early transition metals, which have a higher affinity for forming oxides, carbides, and nitrides. As an advantage over the p-type species, molybdenum is less expensive than the 'nobel' metals such as palladium and platinum, and likely easier to etch. Also, using a single metal for both types presents a processing advantage.

This invention relates in general to organometallic precursor compounds represented by the formula $(L)M(L')_2(NO)$ wherein M is a Group 6 metal, L is a substituted or unsubstituted anionic ligand and L' is the same or different and is a π acceptor ligand. More particularly, this invention relates to organometallic precursor compounds represented by the formula $(L)M(CO)_2(NO)$ wherein M is a Group 6 metal and L is a substituted or unsubstituted anionic ligand. Typically, M is selected from molybdenum, chromium or tungsten, L is selected from a cyclopentadienide, diketonate, amide, cyclic amide, alkoxide, halide or imide, and L' is selected from CO and alkenes. A preferred organometallic precursor compound is represented by the formula $(RL)Mo(CO)_2(NO)$ wherein L is a substituted cyclopentadienyl ligand and R is an alkyl having from 2 to about 8 carbon atoms. Typically, R is selected from ethyl, propyl, isopropyl, butyl, tert-butyl and $SiMe_3$.

This invention also relates to a process for producing an organometallic precursor compound which comprises reacting a Group 6 metal-carbonyl and/or alkene source compound, a hydrocarbon or heteroatom-containing compound and a nitrosyl source compound under reaction conditions sufficient to produce said organometallic precursor compound. Typically, the hydrocarbon or heteroatom-containing compound comprises a lithiated cyclopentadienide, diketonate, amide, cyclic amide, alkoxide, halide or imide.

This invention also relates to a method for producing a film, coating or powder by decomposing an organometallic precursor compound represented by the formula $(L)M(L')_2(NO)$, preferably an organometallic precursor compound represented by the formula $(L)M(CO)_2(NO)$, wherein M is a Group 6 metal, L is a substituted or unsubstituted anionic ligand and L' is the same or different and is a π acceptor ligand, thereby producing the film, coating or powder. Typically, the decomposing of said organometallic precursor compound is thermal, chemical, photochemical or plasma-activated.

The invention has several advantages. For example, the method of the invention is useful in generating organometallic compound precursors that have varied chemical structures and physical properties. Films generated from the organometallic compound precursors can be deposited with a short incubation time, and the films deposited from the organometallic compound precursors exhibit good smoothness.

A preferred embodiment of this invention is that the organometallic precursor compounds may be liquid at room temperature. In some situations, liquids may be preferred over solids from an ease of semiconductor process integration perspective.

As can be seen from this invention, the solution to the problems encountered with the molybdenum-containing precursors of the prior art stems from the addition of a nitrosyl ligand. Although similar to carbonyl (CO) in structure, nitrosyl (NO) is a notably stronger π-acid (by ~1V) when binding in its $NO^+$ form. This fact leads to the second key advantage. Not only does NO stabilize the precursor, e.g., $CpMo(CO)_2(NO)$, by removing excess electron density from the metal center, but the ligand's cationic nature balances the anionic cyclopentadienyl ligand, rendering the overall molecule neutral. This compound is thermally stable, and is only slightly air sensitive (i.e., it can be manipulated for short periods in air). Although the unsubstituted cyclopentadienyl system is a solid, the substituted cyclopentadienyl system is a liquid. Finally, the substituted cyclopentadienyl system appears to have a higher volatility than the bis(ethylbenzene)molybdenum mixture or $Mo(CO)_6$.

In comparison with the methyl substituted cyclopentadienyl compound, i.e., $(MeCp)Mo(CO)_2(NO)$, of the prior art, the organometallic precursor compounds of this invention are typically easier to purify, while the unsubstituted cyclopentadienyl compound, i.e., $CpMo(CO)_2(NO)$, of the prior art forms a solid molybdenum complex. In addition, the organometallic precursor compounds of this invention may be more conducive to the deposition of pure metal films versus compounds such as the molybdenum amides, which have been used for nitrides. However nitrides and oxides may still be accessible with these systems with the proper choice of co-reactant (e.g., ammonia, oxygen, respectively).

DETAILED DESCRIPTION OF THE INVENTION

As indicated above, this invention relates to organometallic precursor compounds represented by the formula $(L)M(L')_2(NO)$, preferably organometallic precursor compounds represented by the formula $(L)M(CO)_2(NO)$, wherein M is a Group 6 metal, L is a substituted or unsubstituted anionic ligand, and L' is the same or different and is a π acceptor ligand. Typically, M is selected from molybdenum, chromium or tungsten, L is selected from a cyclopentadienide, diketonate, amide, cyclic amide, alkoxide, halide or imide, and L' is selected from CO and alkenes. A preferred organometallic precursor compound is represented by the formula $(RL)Mo(CO)_2(NO)$ wherein L is a substituted cyclopentadienyl ligand and R is an alkyl having from 2 to about 8 carbon atoms. Typically, R is selected from ethyl, propyl, isopropyl, butyl, tert-butyl and $SiMe_3$.

Illustrative organometallic precursor compounds of this invention include, for example, $(EtCp)Mo(CO)_2(NO)$, $(PrCp)Mo(CO)_2(NO)$, $(iPrCp)Mo(CO)_2(NO)$, $(BuCp)Mo(CO)_2(NO)$, $(tBuCp)Mo(CO)_2(NO)$, and the like, wherein Et is ethyl, Pr is propyl, iPr is isopropyl, Bu is butyl and tBu is tert-butyl.

As also indicated above, this invention also relates to a process for producing an organometallic precursor compound which comprises reacting a Group 6 metal-carbonyl and/or alkene source compound, e.g., $Mo(CO)_6$ and $Mo(CO)_3(C_2H_4)_3$, a hydrocarbon or heteroatom-containing compound, and a nitrosyl source compound under reaction conditions sufficient to produce said organometallic precursor compound. Typically, the hydrocarbon or heteroatom-containing compound comprises a lithiated cyclopentadienide, diketonate, amide, cyclic amide, alkoxide, halide or imide.

This invention also involves a process for producing an organometallic compound comprising (i) reacting a hydrocarbon or heteroatom-containing material with a base material in the presence of a solvent and under reaction conditions sufficient to produce a first reaction mixture comprising a hydrocarbon or heteroatom-containing compound, (ii) adding a metal-carbonyl and/or alkene source compound and a nitrosyl source compound to said first reaction mixture, (iii) reacting said hydrocarbon or heteroatom-containing compound with said metal-carbonyl and/or alkene source compound and nitrosyl source compound under reaction conditions sufficient to produce a second reaction mixture comprising said organometallic compound, and (iv) separating said organometallic compound from said second reaction mixture. The method is particularly well-suited for large scale production since it can be conducted using the same equipment, some of the same reagents and process parameters that can easily be adapted to manufacture a wide range of products. The method provides for the synthesis of organometallic compounds using a process where all manipulations are carried out in a single vessel, and which route to the organometallic compounds does not require the isolation of an intermediate complex. This method is more fully described in U.S. patent application Ser. No. 10/678,074, filed Oct. 6, 2003, which is incorporated herein by reference.

The organometallic precursor compounds of this invention may also be prepared by conventional methods such as described in Legzdins, P. et al. Inorg. Synth. 1990, 28, 196 and references therein.

The metal-carbonyl and/or alkene source compound, e.g., $Mo(CO)_6$ and $Mo(CO)_3(C_2H_4)_3$, starting material may be selected from a wide variety of compounds known in the art. The invention herein most prefers the Group 6 metals such as molybdenum, chromium and tungsten. The CO ligands are preferred $\pi$ acceptor ligands. Other suitable $\pi$ acceptor ligands include alkenes.

The concentration of the Group 6 metal-carbonyl and/or alkene compound starting material can vary over a wide range, and need only be that minimum amount necessary to react with the hydrocarbon or heteroatom-containing compound and the nitrosyl source compound and to provide the given metal concentration desired to be employed and which will furnish the basis for at least the amount of metal necessary for the organometallic compounds of this invention. In general, depending on the size of the reaction mixture, metal-carbonyl and/or alkene source compound starting material concentrations in the range of from about 1 millimole or less to about 10,000 millimoles or greater, should be sufficient for most processes.

The nitrosyl source compound may be selected from a wide variety of compounds known in the art. Illustrative nitrosyl source compounds include diazald (i.e., N-methyl-N-nitroso-p-toluenesulfonamide), nitrosonium tetrafluoroborate and nitric oxide.

The concentration of the nitrosyl source compound starting material can vary over a wide range, and need only be that minimum amount necessary to react with the metal-carbonyl compound starting material and the hydrocarbon or heteroatom-containing compound. In general, depending on the size of the reaction mixture, nitrosyl source compound starting material concentrations in the range of from about 1 millimole or less to about 10,000 millimoles or greater, should be sufficient for most processes.

The hydrocarbon or heteroatom-containing starting material may be selected from a wide variety of compounds known in the art. Illustrative hydrocarbon or heteroatom-containing compounds include, for example, amines, alcohols, diketones, cyclopentadienes, imines, hydrocarbons, halogens and the like. Preferred hydrocarbon or heteroatom-containing starting materials include alkyl substituted cyclopentadienes including their alkali metal salts, for example, LiEtCp.

The concentration of the hydrocarbon or heteroatom-containing starting material can vary over a wide range, and need only be that minimum amount necessary to react with the base starting material. In general, depending on the size of the reaction mixture, hydrocarbon or heteroatom-containing starting material concentrations in the range of from about 1 millimole or less to about 10,000 millimoles or greater, should be sufficient for most processes.

The base starting material may be selected from a wide variety of compounds known in the art. Illustrative bases include any base with a pKa greater than about 10, preferably greater than about 20, and more preferably greater than about 25. The base material is preferably n-BuLi, t-BuLi, MeLi, NaH, CaH, lithium amides and the like.

The concentration of the base starting material can vary over a wide range, and need only be that minimum amount necessary to react with the hydrocarbon or heteroatom-containing starting material. In general, depending on the size of the first reaction mixture, base starting material concentrations in the range of from about 1 millimole or less to about 10,000 millimoles or greater, should be sufficient for most processes.

In one embodiment, the hydrocarbon or heteroatom-containing compound may be generated in situ, for example, lithiated amides, alkoxides, diketonates, cyclopentadienides, imides and the like. Generating the hydrocarbon or heteroatom-containing compound in situ in the reaction vessel immediately prior to reaction with the metal source compound is beneficial from a purity standpoint by eliminating the need to isolate and handle any reactive solids. It is also less expensive.

With the in situ generated hydrocarbon or heteroatom-containing compound in place, addition of the metal-carbonyl source compound, e.g., $Mo(CO)_6$, can be performed through solid addition, or in some cases more conveniently as a solvent solution or slurry. Although certain metal-carbonyl source compounds are moisture sensitive and are used under an inert atmosphere such as nitrogen, it is generally to a much lower degree than the hydrocarbon or heteroatom-containing compounds, for example, lithiated amides, alkoxides, diketonates, cyclopentadienides, imides and the like. Furthermore, many metal-carbonyl source compounds such as $Mo(CO)_6$ are denser and easier to transfer.

The hydrocarbon or heteroatom-containing compounds prepared from the reaction of the hydrocarbon or heteroatom-containing starting material and the base starting material may be selected from a wide variety of compounds known in the art. Illustrative hydrocarbon or heteroatom-containing compounds include, for example, lithiated amides, alkoxides, diketonates, cyclopentadienides, imides and the like.

The concentration of the hydrocarbon or heteroatom-containing compounds can vary over a wide range, and need only be that minimum amount necessary to react with the metal-carbonyl source compounds and nitrosyl-source compounds to give the organometallic compounds of this invention. In general, depending on the size of the reaction mixture, hydrocarbon or heteroatom-containing compound concentrations in the range of from about 1 millimole or less to about 10,000 millimoles or greater, should be sufficient for most processes.

The solvent employed in the method of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitrites, silicone oils, other aprotic solvents, or mixtures of one or more of the above; more preferably, diethylether, pentanes, or dimethoxyethanes; and most preferably hexanes or THF. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the base starting material with the hydrocarbon or heteroatom-containing material, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

Reaction conditions for the reaction of the hydrocarbon or heteroatom-containing compound with the metal-carbonyl and/or alkene source compound and the nitrosyl source compound, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps. In the embodiment of this invention which is carried out in a single pot, the hydrocarbon or heteroatom-containing compound is not separated from the first reaction mixture prior to reacting with the metal-carbonyl and/or alkene source compound. In a preferred embodiment, the metal-carbonyl source compound is added to the first reaction mixture at ambient temperature or at a temperature greater than ambient temperature.

The organometallic compounds prepared from the reaction of the hydrocarbon or heteroatom-containing compound, the metal-carbonyl and/or alkene source compound and the nitrosyl source compound may be selected from a wide variety of compounds known in the art. For purposes of this invention, organometallic compounds include compounds having a metal-carbon atom bond as well as compounds having a metal-heteroatom bond. Illustrative organometallic compounds include, for example, Group 6 metal-containing amides, alkoxides, diketonates, cyclopentadienides, halides, imides and the like.

For organometallic compounds prepared by the method of this invention, purification can occur through recrystallization, more preferably through extraction of reaction residue (e.g., hexane) and chromatography, and most preferably through sublimation and distillation.

Furthermore, this process is not limited to molybdenum-cyclopentadiene based systems. It can also be extended to other metals as well as other anionic ligands. Examples of other metals include, but are not limited to, chromium and tungsten. Other ligands include, but are not limited to, alkoxides, betadiketonates, imides, nitrates, anionic hydrocarbons, halides, carbonates and the like.

Those skilled in the art will recognize that numerous changes may be made to the method described in detail herein, without departing in scope or spirit from the present invention as more particularly defined in the claims below.

Examples of techniques that can be employed to characterize the organometallic compounds formed by the synthetic methods described above include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organometallic compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

Many organometallic compound precursors described herein are liquid at room temperature and are well suited for preparing in-situ powders and coatings. For instance, a liquid organometallic compound precursor can be applied to a substrate and then heated to a temperature sufficient to decompose the precursor, thereby forming a metal or metal oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Liquid organometallic compound precursors such as described above also can be atomized and sprayed onto a substrate. Atomization and spraying means, such as nozzles, nebulizers and others, that can be employed are known in the art.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organometallic compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone ($O_3$), nitrous oxide ($N_2O$), water vapor, organic vapors, ammonia and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

As indicated above, this invention also relates in part to a process for producing a film, coating or powder. The process includes the step of decomposing at least one organometallic compound precursor, thereby producing the film, coating or powder, as further described below.

Deposition processes described herein can be conducted to form a film, powder or coating that includes a single metal or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the organometallic compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of molybdenum, for instance, can be considered for fabricating metal electrodes, in particular as n-channel metal electrodes in logic, as capacitor electrodes for DRAM applications, and as dielectric materials.

The process also is suited for preparing layered films, wherein at least two of the layers differ in phase or composition. Examples of layered film include metal-insulator-semiconductor, and metal-insulator-metal.

In an embodiment, the invention is directed to a process that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metalorganic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The process of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the process of the invention include solid substrates such as metal substrates, e.g., Al, Ni, Ti, Co, Pt, Ta; metal suicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The process of the invention can be conducted to deposit a film on a substrate that has a smooth, flat surface. In an embodiment, the process is conducted to deposit a film on a substrate used in wafer manufacturing or processing. For instance, the process can be conducted to deposit a film on patterned substrates that include features such as trenches, holes or vias. Furthermore, the process of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometer and more preferably less than 200 nanometers thick. Films that are less than 50 nanometer thick, for instance, films that have a thickness between about 1 and about 20 nanometers, also can be produced.

Organometallic compound precursors described above also can be employed in the process of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The process of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal or metal oxide film. As described above an organometallic compound precursor can be used alone or in combination with one or more components, such as, for example, other organometallic precursors, inert carrier gases or reactive gases.

In a system that can be used in producing films by the process of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal oxide. Mixed films also can be deposited, for instance mixed metal oxide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Various modifications and variations of this invention will be obvious to a worker skilled in the art and it is to be understood that such modifications and variations are to be included within the purview of this application and the spirit and scope of the claims.

EXAMPLE 1

In a glovebox, $Mo(CO)_6$ (31.9 grams, 121 mmol) was placed into a three-neck 500 milliliter round-bottom flask containing a stir bar. Also in the glovebox, Li(EtCp) (11.5 grams, 115 mmol) was placed into a one-neck 250 milliliter round-bottom flask. To each flask was added 150 milliliters of anhydrous inhibitor-free THF, and each was capped with septa. The flasks were removed from the box and placed in a fume hood. The flask containing the molybdenum reagent was placed into a heating mantle above a stir plate and clamped into position. A nitrogen inlet and an exhaust line (through an oil bubbler at the top rear of the hood) were placed into the side-neck septum via needles. Under a heavy nitrogen purge (i.e., vigorous bubbling in the oil bubbler) the center-neck septa was removed and a water condenser was attached. Water flow was initiated (through a 'fail-safe' turn wheel device hooked up to the variac for the heating mantle to discontinue heating if water fails), and the inlet and outlet lines were copper wired. The top of the condenser was fitted with a 24/40 t-joint. After a few minutes, the nitrogen/exhaust lines were removed from the septum and attached (with no needles) to the two t-joint hose barbs (using copper wire). Stirring was commenced.

The Li(EtCp) solution was transferred to the reaction flask by cannula via pressure transfer. After addition was complete, the two flask septa were replaced with pennyhead stoppers under a heavy purge. Heating was commenced, and the mixture was brought to reflux under a slow purge of nitrogen through the t-joint. Reflux was continued for 43 hours (during which time CO gas will evolve and exhaust through the bubbler). The mixture was then allowed to cool to room temperature. While the mixture was cooling, in the glovebox was prepared a solution of Diazald (i.e., N-methyl-N-nitroso-p-toluenesulfonamide) (25.0 grams, 115 mmol) in THF (100 milliliters) within a one-neck 150 milliliter round bottom flask. The flask was capped with a septum and brought into the fume hood. The contents of the flask were transferred slowly (45 minutes) to the stirring room temperature reaction mixture by pressure transfer via cannula (note: CO evolution will occur quickly, releasing approximately 3 liters of CO). Once the Diazald addition was complete, stirring was continued for 1 hour, after which the condenser was removed, and the contents of the flask were filtered in the fume hood through a medium porosity frit.

The remaining solids were rinsed with THF (4×25 milliliters). The filtrate was placed into a 1 liter round-bottom flask and the solvent removed in vacuo (rotovap with $N_2$ refill). The remaining liquid was loaded onto a 500 milliliter frit loaded halfway with silica gel with a 2 centimeter layer of sand on top. The plug was eluted with pentane. After an initial 500 milliliter of colorless pentane was recovered, 2 liters of orange product solution was collected (note: the pentane solution 'filtrate' was still orange when collection was halted). The solvent was removed from the product solution in-vacuo (rotovap with $N_2$ refill) and the remaining liquid was transferred to a 100 milliliter round-bottom flask for distillation (crude yield 28.5 grams, 90%). The product was vacuum distilled on a short path apparatus. An early sublimate fraction (crystalline pale yellow solid) was recovered initially and discarded (after NMR analysis). The desired product was then collected in a new receiver flask (pot temperature 120° C., head temperature 70° C., 0.15 torr line gauge). $(EtCp)Mo(CO)_2(NO)$, 25.8 grams (82%), is a vivid orange liquid. $(EtCp)Mo(CO)_2(NO)$ may be handled for short periods in air, but is best stored under nitrogen. The compound was characterized and proven to be >99% pure by NMR, GC-MS/FID, and TGA. Melting point (−10° C.) was determined by DSC.

The invention claimed is:
1. An organometallic precursor compound represented by the formula $(RL)Mo(CO)_2(NO)$ wherein L is a substituted cyclopentadienyl ligand and R is an alkyl having from 2 to about 8 carbon atoms.

2. The organometallic precursor compound of claim 1 wherein R is selected from ethyl, propyl, isopropyl, butyl, tert-butyl and SiMe$_3$.

3. The organometallic precursor compound of claim 1 which is selected from (EtCp)Mo(CO)$_2$(NO), (PrCp)Mo(CO)$_2$(NO), (iPrCp)Mo(CO)$_2$(NO), (BuCp)Mo(CO)$_2$(NO), (tBuCp)Mo(CO)$_2$(NO), and the like, wherein Et is ethyl, Pr is propyl, iPr is isopropyl, Bu is butyl and tBu is tert-butyl.

4. A process for producing an organometallic precursor compound which comprises reacting a Group 6 metal-carbonyl or alkene source compound, a hydrocarbon or heteroatom-containing compound and a nitrosyl source compound under reaction conditions sufficient to produce said organometallic precursor compound, wherein the organometallic precursor compound is selected from (EtCp)Mo(CO)$_2$(NO), (PrCp)Mo(CO)$_2$(NO), (iPrCp)Mo(CO)$_2$(NO), (BuCp)Mo(CO)$_2$(NO), (tBuCp)Mo(CO)$_2$(NO) and the like, wherein Et is ethyl, Pr is propyl, iPr is isopropyl, Bu is butyl and tBu is tert-butyl.

5. An organometallic precursor compound represented by the formula (RL)M(L')$_2$(NO) wherein M is a Group 6 metal, L is a substituted cyclopentadienyl ligand, L' is the same or different and is a π acceptor ligand, and R is an alkyl having from 2 to about 8 carbon atoms or SiMe3.

6. The organometallic precursor compound of claim 5 wherein R is selected from ethyl, propyl, isopropyl, butyl, tert-butyl.

7. The organometallic precursor compound of claim 5 wherein M is selected from molybdenum, chromium or tungsten.

8. The organometallic precursor compound of claim 5 which is selected from (EtCp)Mo(CO)$_2$(NO), (PrCp)Mo(CO)$_2$(NO), (iPrCp)Mo(CO)$_2$(NO), (BuCp)Mo(CO)$_2$(NO), (tBuCp)Mo(CO)$_2$(NO), and the like, wherein Et is ethyl, Pr is propyl, iPr is isopropyl, Bu is butyl and tBu is tert-butyl.

9. An organometallic precursor compound represented by the formula (RL)M(CO)$_2$(NO) wherein M is a Group 6 metal, L is a substituted cyclopentadienyl ligand and R is an alkyl having from 2 to about 8 carbon atoms.

10. The organometallic precursor compound of claim 9 wherein R is selected from ethyl, propyl, isopropyl, butyl, tert-butyl and SiMe$_3$.

11. The organometallic precursor compound of claim 9 wherein M is selected from molybdenum, chromium or tungsten.

12. The organometallic precursor compound of claim 9 which is selected from (EtCp)Mo(CO)$_2$(NO), (PrCp)Mo(CO)$_2$(NO), (iPrCp)Mo(CO)$_2$(NO), (BuCp)Mo(CO)$_2$(NO), (tBuCp)Mo(CO)$_2$(NO), and the like , wherein Er is ethyl, Pr is propyl, iPr is isopropyl, Bu is butyl and tBu is tert-butyl.

13. An organometallic precursor compound represented by the formula (L)M(L')$_2$(NO) wherein M is a Group 6 metal, L is a substituted or unsubstituted anionic ligand selected from a diketonate, amide, cyclic amide, alkoxide, halide or imide, and L' is the same or different and is a π acceptor ligand.

14. The organometallic precursor compound of claim 13 represented by the formula (L)M(CO)$_2$(NO) wherein M is a Group 6 metal and L is a substituted or unsubstituted anionic ligand selected from a diketonate, amide, cyclic amide, alkoxide, halide or imide.

15. The organometallic precursor compound of claim 13 wherein M is selected from molybdenum, chromium or tungsten.

16. An organometallic precursor compound represented by the formula (L)Mo(L')(NO) wherein L is a substituted or unsubstituted anionic ligand selected from a diketonate, amide, cyclic amide, alkoxide, halide or imide, and L' is the same or different and is a π acceptor ligand.

17. The organometallic precursor compound of claim 16 represented by the formula (L)Mo(CO)$_2$(NO) wherein L is a substituted or unsubstituted anionic ligand selected from a diketonate, amide, cyclic amide, alkoxide, halide or imide.

18. A process for producing an organometallic precursor compound which comprises reacting a Group 6 metal-carbonyl or alkene source compound, a hydrocarbon or heteroatom-containing compound and a nitrosyl source compound under reaction conditions sufficient to produce said organometallic precursor compound, wherein said organometallic precursor compound is represented by the formula (RL)M(L')$_2$(NO) in which M is a Group 6 metal, L is a substituted cyclopentadienyl ligand, L' is the same or different and is a π acceptor ligand, and R is an alkyl having from 2 to about 8 carbon atoms or SiMe3.

19. The process of claim 18 wherein said hydrocarbon or heteroatom-containing compound comprises a lithiated cyclopentadienide.

20. The process of claim 18 wherein R is selected from ethyl, propyl, isopropyl, butyl, tert-butyl.

21. The process of claim 18 wherein M is selected from molybdenum, chromium or tungsten.

22. The process of claim 18 wherein the organometallic precursor compound is selected from (EtCp)Mo(CO)$_2$(NO), (PrCp)Mo(CO)$_2$(NO), (iPrCp)Mo(CO)$_2$(NO), (BuCp)Mo(CO)$_2$(NO), (tBuCp)Mo(CO)$_2$(NO), and the like, wherein Et is ethyl, Pr is propyl, iPr is isopropyl, Bu is butyl and tBu is tert-butyl.

23. A process for producing an organometallic precursor compound which comprises reacting a Group 6 metal-carbonyl or alkene source compound, a hydrocarbon or heteroatom-containing compound and a nitrosyl source compound under reaction conditions sufficient to produce said organometallic precursor compound, wherein said organometallic precursor compound is represented by the formula (RL)M(CO)$_2$(NO) in which M is a Group 6 metal, L is a substituted cyclopentadienyl ligand and R is an alkyl having from 2 to about 8 carbon atoms or SiMe3.

24. The process of claim 23 wherein said hydrocarbon or heteroatom-containing compound comprises a lithiated cyclopentadienide.

25. The process of claim 23 wherein R is selected from ethyl, propyl, isopropyl, butyl, tert-butyl.

26. The process of claim 23 wherein M is selected from molybdenum, chromium or tungsten.

27. The process of claim 23 wherein the organometallic precursor compound is selected from (EtCp)Mo(CO)$_2$(NO), (PrCp)Mo(CO$_2$(NO), (iPrCp)Mo(CO)$_2$(NO), (BuCp)Mo(CO)$_2$(NO), (tBuCp)Mo(CO)$_2$(NO), and the like, wherein Et is ethyl, Pr is propyl, iPr is isopropyl, Bu is butyl and tBu is tert-butyl.

28. A process for producing an organometallic precursor compound which comprises reacting a Group 6 metal-carbonyl or alkene source compound, a hydrocarbon or heteroatom-containing compound and a nitrosyl source compound under reaction conditions sufficient to produce said organometallic precursor compound, wherein said organometallic precursor compound is represented by the formula (RL)Mo(CO)$_2$(NO) wherein L is a substituted cyclopentadienyl ligand and R is an alkyl having from 2 to about 8 carbon atoms or SiMe3.

29. The process of claim 28 wherein said hydrocarbon or heteroatom-containing compound comprises a lithiated cyclopentadienide.

30. The process of claim 28 wherein R is selected from ethyl, propyl, isopropyl, butyl, tert-butyl.

31. The process of claim 28 wherein the organometallic precursor compound is selected from (EtCp)Mo(CO)$_2$(NO), (PrCp)Mo(CO)$_2$(NO), (iPrCp)Mo(CO)$_2$(NO), (BuCp)Mo(CO)$_2$(NO), (tBuCp)Mo(CO)$_2$(NO), and the like, wherein Et is ethyl, Pr is propyl, ipr is isopropyl, Bu is butyl and tBu is ten-butyl.

32. A process for producing an organometallic precursor compound which comprises reacting a Group 6 metal-carbonyl or alkene source compound, a hydrocarbon or heteroatom-containing compound and a nitrosyl source compound under reaction conditions sufficient to produce said organometallic precursor compound, wherein said organometallic precursor compound is represented by the formula (L)M(L')$_2$(NO) in which M is a Group 6 metal, L is a substituted or unsubstituted anionic ligand selected from a diketonate, amide, cyclic amide, alkoxide, halide or imide, and L' is the same or different and is a π acceptor ligand.

33. The process of claim 32 wherein said organometallic precursor compound is represented by the formula (L)M(CO)$_2$(NO) in which M is a Group 6 metal and L is a substituted or unsubstituted anionic ligand selected from a diketonate, amide, cyclic amide, alkoxide, halide or imide.

34. The process of claim 32 wherein said hydrocarbon or heteroatom-containing compound comprises a lithiated diketonate, amide, cyclic amide, alkoxide, halide or imide.

35. The process of claim 32 wherein M is selected from molybdenum, chromium or tungsten.

36. The process of claim 32 wherein the organometallic precursor compound is selected from (EtCp)Mo(CO)$_2$(NO), (PrCp)Mo(CO)$_2$(NO), (iPrCp)Mo(CO)$_2$(NO), (BuCp)Mo(CO)$_2$(NO), (tBuCp)Mo(CO)$_2$(NO), and the like, wherein Et is ethyl, Pr is propyl, iPr is isopropyl, Bu is butyl and tBu is tert-butyl.

37. A process for producing art organometallic precursor compound which comprises reacting a Group 6 metal-carbonyl or alkene source compound, a hydrocarbon or heteroatom-containing compound and a nitrosyl source compound under reaction conditions sufficient to produce said organometallic precursor compound, wherein said organometallic precursor compound is represented by the formula (L)Mo(L')$_2$(NO) wherein L is a substituted or unsubstituted anionic ligand selected from a diketonate, amide, cyclic amide, alkoxide, halide or imide, and L' is the same or different and is a π acceptor ligand.

38. The process of claim 37 represented wherein said organometallic precursor compound is by the formula (L)Mo(CO)$_2$(NO) in which L is a substituted or unsubstituted anionic ligand selected from a diketonate, amide, cyclic amide, alkoxide, halide or imide.

39. The process of claim 37 wherein said hydrocarbon or heteroatom-containing compound comprises a lithiated diketonate, amide cyclic amide, alkoxide, halide or imide.

40. The process of claim 37 wherein the organometallic precursor compound is selected from (EtCp)Mo(CO)$_2$(NO), (PrCp)Mo(CO)$_2$(NO), (iPrCp)Mo(CO)$_2$(NO), (BuCp)Mo(CO)$_2$(NO), (tBuCp)Mo(CO)$_2$(NO), and the like, wherein Et is ethyl, Pr is propyl, iPr is isopropyl, Bu is butyl and tBu is tert-butyl.

* * * * *